United States Patent
Hisamatsu et al.

(10) Patent No.: US 6,485,457 B1
(45) Date of Patent: Nov. 26, 2002

(54) CATHETER

(75) Inventors: Takatomo Hisamatsu, Fujinomiya (JP); Toshinobu Ishida, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 136 days.

(21) Appl. No.: 09/669,885

(22) Filed: Sep. 27, 2000

(30) Foreign Application Priority Data

Sep. 28, 1999  (JP) ............................................. 11-274379

(51) Int. Cl.⁷ ............................................. A61M 25/04
(52) U.S. Cl. ........................... 604/102.02; 604/103.09; 604/524; 604/527
(58) Field of Search ................................. 604/523, 524, 604/525, 526, 527, 528, 533, 102.02, 102.03, 102.04, 103.09; 606/194

(56) References Cited

U.S. PATENT DOCUMENTS

| | | | |
|---|---|---|---|
| 4,762,129 A | 8/1988 | Bonzel | 128/344 |
| 5,040,548 A | 8/1991 | Yock | 128/898 |
| 5,061,273 A | 10/1991 | Yock | 606/194 |
| 5,135,535 A | 8/1992 | Kramer | 606/194 |
| 5,217,482 A | 6/1993 | Keith | 606/194 |
| 5,334,169 A * | 8/1994 | Brown et al. | 604/265 |
| 5,410,797 A | 5/1995 | Steinke et al. | 29/435 |
| 5,425,711 A | 6/1995 | Ressemann et al. | 604/96 |
| 5,538,513 A * | 7/1996 | Okajima | 138/124 |
| 5,549,556 A | 8/1996 | Ndondo-Lay et al. | 604/102 |
| 5,891,110 A | 4/1999 | Larson et al. | 604/280 |
| 5,906,606 A * | 5/1999 | Chee et al. | 604/246 |
| 6,036,670 A * | 3/2000 | Wijeratne et al. | 604/526 |
| 6,186,978 B1 * | 2/2001 | Samson et al. | 604/525 |

FOREIGN PATENT DOCUMENTS

| | | |
|---|---|---|
| EP | 0 778 037 | 6/1997 |
| EP | 0 861 674 | 9/1998 |
| EP | 0 925 801 | 6/1999 |

* cited by examiner

Primary Examiner—William E. Tapolcai
(74) Attorney, Agent, or Firm—Burns, Doane, Swecker & Mathis, LLP

(57) ABSTRACT

A catheter includes a tubular proximal shaft having relatively high rigidity, a tubular distal shaft having rigidity lower than that of the proximal shaft, a tubular intermediate section disposed between the proximal shaft and the distal shaft, a hub arranged near a proximal end of the proximal shaft, a balloon provided to a distal portion of the distal shaft to be in fluid communication, and a guide wire lumen having a distal aperture located on a distal end side of the distal end of the balloon and a proximal aperture located on a proximal end side of the proximal end of the balloon, through which a guide wire is inserted, wherein a reinforcing member consisting of a braided member made of at least one linear member, is embedded in the intermediate section. The catheter is capable of effectively avoiding kink caused by heavy concentration of flexural stress.

16 Claims, 3 Drawing Sheets

CATHETER

CROSS-REFERENCE TO RELATED APPLICATIONS

This application is based upon and claims the benefit of priority from the prior Japanese Patent Application No. 11-274379, filed Sep. 28, 1999, the entire contents of which are incorporated herein by reference.

BACKGROUND OF THE INVENTION

The present invention relates to a catheter such as a balloon catheter, or an intravascular therapeutic or diagnostic catheter.

In accordance with the development of the microcatheter, it becomes possible to perform microvascular or intravascular therapy and diagnosis, which has been considered impossible with conventional catheters. Examples of the microcatheter are catheters for percutaneous transluminal coronary angioplasty, used for cardiac infarction or angia pertoris (referred to as a balloon catheter hereinafter). In the operation of angioplasty, it is necessary to exchange one catheter for another many times. The catheter must be exchanged, for example, when the balloon size is changed or a diagnostic or treatment device for diagnosing or treating a vicinity of a stenosed portion is changed. As an example of the method of exchanging a catheter, there is a conventionally known technique in which a long exchange guide wire is used. However, it requires not only a long period of time to handle such a long wire, but also at least two operators for the operation, and therefore the handling of the wire is not easy. In order to solve this drawback, a so-called "rapid exchange" type catheter has been proposed. The catheter of this type has a structure in which only the distal portion thereof tracks the guide wire.

Examples of the catheter of the rapid-exchange type are discussed in U.S. Pat. Nos. 5,040,548, 5,061,273 (to Yock), U.S. Pat. No. 4,762,129 (to Bonzel), U.S. Pat. No. 5,135,535 (to Kramer) and the like.

Here, the rapid-exchange type catheter disclosed in PCT Publication WO93/15786 will now be described in detail. This catheter consists of a proximal shaft, a distal shaft, a balloon and a tube for guide wire lumen, and a core wire which extends in the direction of the distal shaft, is bonded to the proximal shaft. The core wire imparts rigidity to the distal shaft having a relatively low rigidity, which is attached to the distal side of the proximal shaft having a relatively high rigidity. In this manner, kinking in the distal shaft due to heavy concentration of flexural stress, can be prevented.

However, in this catheter, the core wire is present inside the inflation lumen, which narrows the cross sectional area of the inflation lumen. This causes the problem of inhibiting of shortening the balloon inflation/deflating time. As a result, the time for stemming the blood flow during the inflation of the balloon is prolonged, putting stress on a patient. Not only the rapid-exchange type catheter has such a drawback, but it is also common to all the catheters of the type in which a core wire is installed in a flow path as a reinforcing member.

In the meantime, PCT Publication WO92/03178 discloses a rapid-exchange catheter having such a structure that an intermediate sleeve section is provided between a proximal shaft made of a metal tube and a distal shaft having high flexibility, and a coil member is provided around the outer circumference of the sleeve section for reinforcement.

However, even if a coil member is provided around the outer circumference of the intermediate sleeve section, it is not possible to effectively avoid kinking caused by heavy concentration of flexural stress. The coil member is would in only one direction toward the distal end of the catheter, and therefore as the operator rotates the catheter in an opposite direction while gripping the hub, the wound coil is loosened and accordingly gaps between adjacent coil wires are widened, thereby causing deterioration of the kink resistance. Moreover, because the intermediate sleeve section is superfluously bent due to the loosening of the coil, there may be caused a problem that torque or pushing force, which is provided on the proximal end of the catheter, is hard to be surely transmitted to the distal end of the catheter.

BRIEF SUMMARY OF THE INVENTION

The object of the present invention is to provide a catheter capable of effectively avoiding kink caused by heavy concentration of flexural stress, without narrowing cross sectional area of the inflation lumen.

A balloon catheter of the present invention includes: a tubular proximal shaft having a relatively high rigidity; a tubular distal shaft having rigidity lower than that of the proximal shaft; a tubular intermediate section disposed between the proximal shaft and the distal shaft; a hub arranged near a proximal end of the proximal shaft, to which a pressure applying device is attached; a balloon provided to a distal portion of the distal shaft to be in fluid communication, to which pressure is applied from the hub; and a guide wire lumen having a distal aperture located on a distal end side of the distal end of the balloon and a proximal aperture located on a further proximal end side of the proximal end of the balloon, through which a guide wire is inserted; wherein a reinforcing member consisting of a braided member formed by braiding at least one linear member, is embedded in the intermediate section.

A catheter of the present invention includes: a proximal shaft having relatively high rigidity; a distal shaft having rigidity lower than that of the proximal shaft; an intermediate section disposed between the proximal shaft and the distal shaft; a hub arranged near a proximal end of the proximal shaft; a treatment device (device for therapy or diagnose, such as an ultrasonic diagnostic device, a laser, an atherectomy cutter, a medicine supply device, a radio frequency generator or an ultrasonic therapy device) attached on a distal portion of the distal shaft; and a guide wire lumen having a distal aperture located on a distal end side of the treatment device and a proximal aperture located on a proximal end side of the proximal end of the treatment device, through which a guide wire is inserted; wherein a reinforcing member consisting of a braided member formed by braiding at least one linear member, is embedded in the intermediate section.

In the present invention, it is preferable that the distal shaft having relatively high rigidity should be made of a metal tube. Further, the present invention may be of a structure in which the intermediate section has an inner layer and an outer layer, and the reinforcing member is embedded between the inner surface and outer surface of the intermediate section, or of a structure in which the reinforcing member is embedded in the intermediate section such that it is exposed to an internal lumen of the intermediate section.

It is preferable in the present invention that the reinforcing member should be made by braiding linear member(s) such that there are sections where the inclination angles of the linear member(s) which constituting the reinforcing member are relatively large and relatively small with respect to the axial direction of the intermediate section.

According to the catheter of the present invention, the cross section of the inflation lumen is not narrowed and therefore the balloon inflation/deflation time is not prolonged, unlike in the prior art where the core wire is used. Therefore, it becomes possible to reduce the stress on a patient. Further, the reinforcing member which is made of a braided member exhibits a greater effect of preventing kink, than in the case of a reinforcing member made of a conventional coil member. Furthermore, when the reinforcing member is made by braiding at least one linear member such that there are sections where the inclination angles of the linear member(s) constituting the reinforcement member are relatively large and relatively small with respect to the axial direction of the intermediate section, it becomes possible to vary the rigidity of the shaft gradually. Consequently, the kink can be more efficiently avoided.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment of a balloon catheter of the present invention will now be described with reference to accompanying drawings.

Figure 1:
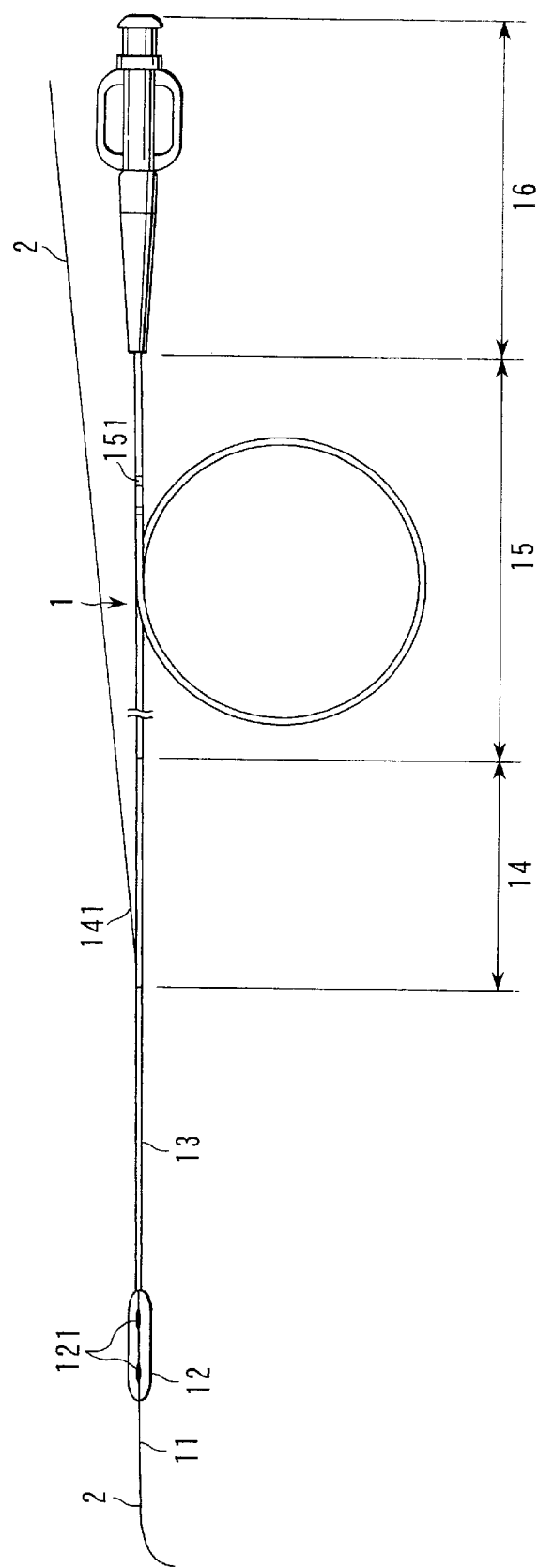
FIG. 1 is a diagram showing a balloon catheter according to an embodiment of the present invention.
Figure 2:
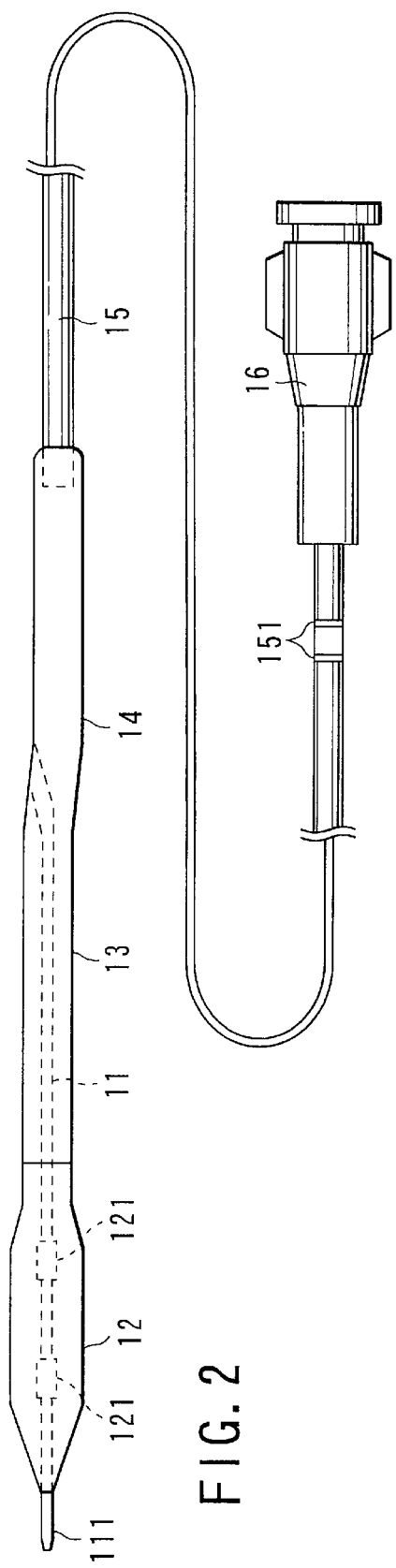
FIG. 2 is an enlarged view of main structural members of the balloon catheter shown in FIG. 1.
Figure 3:
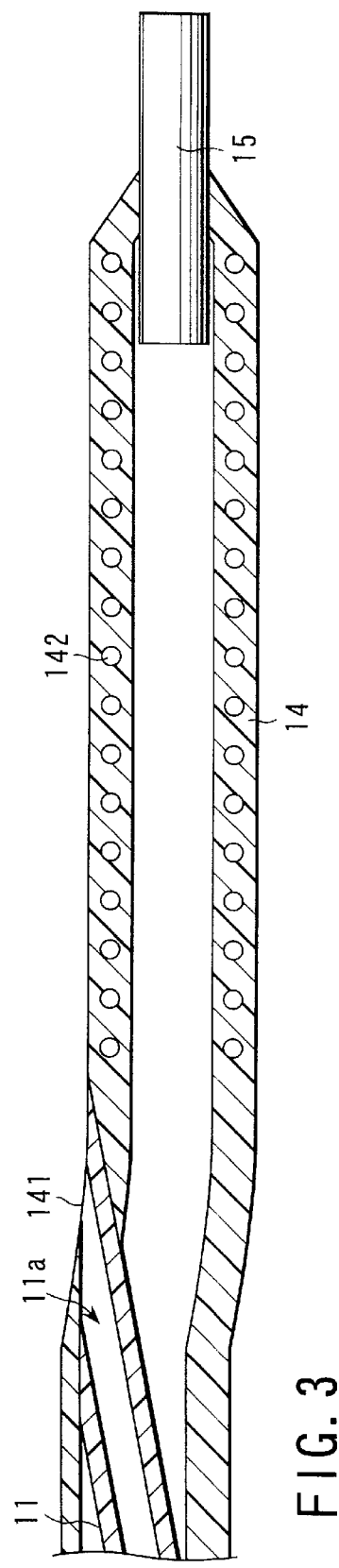
FIG. 3 is a cross sectional view showing the intermediate section, the distal end portion of the proximal shaft, and the proximal end portion of the distal shaft of the balloon catheter shown in FIG. 1.
Figure 4A:
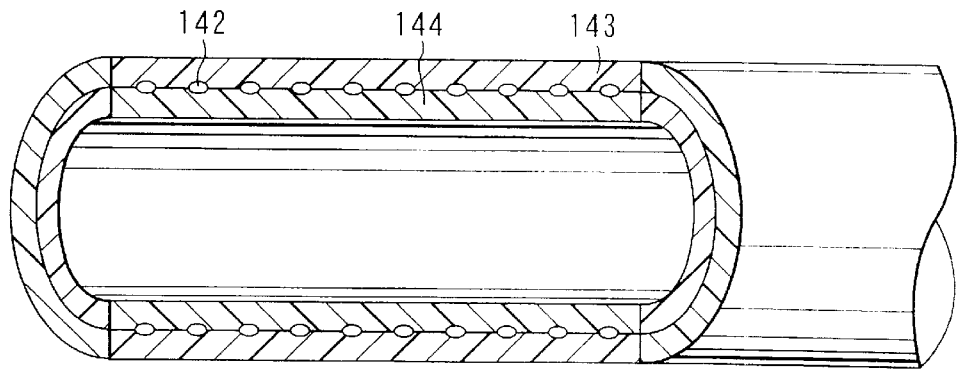
FIGS. 4A and 4B are respectively a cross sectional view illustrating an example of arrangement of a reinforcing member in the intermediate section, and a perspective view thereof.
Figure 4B:
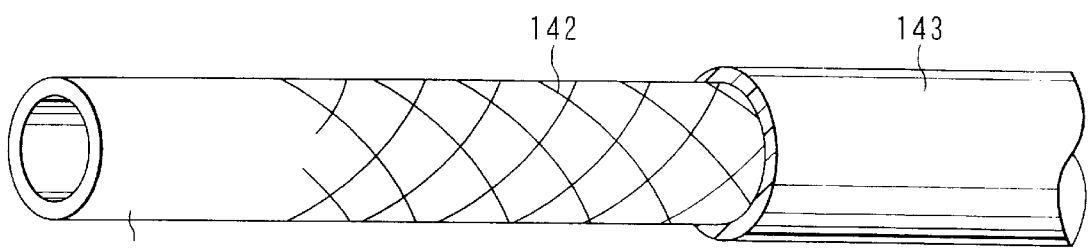
Figure 5A:
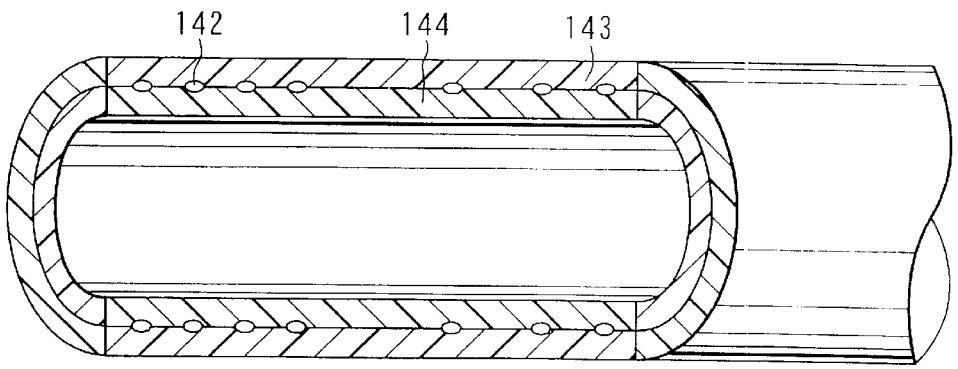
FIGS. 5A and 5B are respectively a cross sectional view illustrating another example of arrangement of a reinforcing member in the intermediate section, and a perspective view thereof.
Figure 5B:
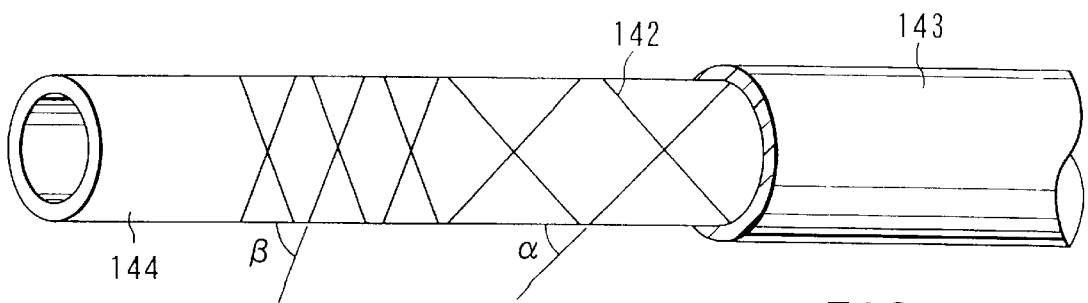

FIG. 1 is a perspective view of a balloon catheter according to an embodiment of the present invention. FIG. 2 is a partially cutaway view of the balloon catheter shown in FIG. 1, in which a part of the proximal shaft is omitted and the main structural members are enlarged. FIG. 3 is a cross sectional view showing the intermediate section, the distal end portion of the proximal shaft and the proximal end portion of the distal shaft. FIGS. 4A and 4B are respectively a more detailed cross sectional view illustrating arrangement of a reinforcing member in the intermediate section, and a perspective view thereof. FIGS. 5A and 5B are respectively a cross sectional view illustrating another example of arrangement of a reinforcing member in the intermediate section, and a perspective view thereof.

As shown in FIGS. 1 and 2, a balloon catheter 1 is a so-called over-the-wire catheter, and it is inserted into a blood vessel along the guide wire 2. The balloon catheter 1 includes, from its proximal end side, a hub 16, a proximal shaft 15, an intermediate section 14, a distal shaft 13, a balloon 12 and an inner shaft 11. The balloon catheter shown in these figures is a rapid exchange type catheter. A guide wire aperture 141 is made at a location a predetermined distance away from the distal end of the proximal end shaft 15, and only the portion situated on the distal end side from the aperture 141 tracks the guide wire.

A lure taper is formed on the hub 16 of the proximal end side, so as to make it connectable with a pressure applying device such as an inflator. To the hub 16, the proximal end shaft 15 made of a metal or a type of resin having relatively high rigidity is bounded so as to be in fluid communication. The proximal shaft 15 is provided with a depth marker 151, with which it can be easily detected how deep the balloon catheter 1 is inserted along a guiding catheter (not shown) during an angioplasty.

The intermediate section 14 is provided on the distal end side of the proximal shaft 15 so as to be in fluid communication with the proximal shaft section 15. Further, to the distal end side of the intermediate section 14, the distal shaft 15 made of a material having relatively low rigidity, such as resin, is provided so as to be in fluid communication with the intermediate section 14. FIG. 3 shows a structure of the distal end portion of the proximal shaft 15 and the proximal end of the distal shaft 13, together with the intermediate section 14 at the center. As shown in this figure, a reinforcing member 142 made of a braided member, formed by braiding at least one linear member, is embedded in the intermediate section 14. The structure of the intermediate section 14 will be described later in detail.

The proximal end portion of the balloon 12 is bounded to the distal end side of the distal shaft 13 so as to be in fluid communication with the distal shaft 13. The inner shaft 11 is pierced coaxially through the distal shaft 13 and the balloon 12. The distal end portion of the inner shaft 11 is formed into a distal end chip 111, and the distal end chip 111 is extended from the distal end of the balloon 12. Thus, the distal end chip 111 is bounded to the distal end side of the balloon 12 in a fluid-tight state. On the other hand, the proximal end of the inner shaft 11 is extended to the guide wire aperture 141 provided in a portion of the intermediate section 14 or the distal shaft 13, and bounded to the portion in a fluid-tight state. More specifically, the proximal end of the inner shaft 11 is fixed to a portion of the intermediate section 14 in an outer circumferential, and a proximal end aperture of the inner shaft 11 is exposed to outside of the intermediate section 14, thus forming the guide wire aperture 141. It should be noted that the guide wire aperture 141 may be provided in the proximal shaft 15 or the distal shaft 13, or even in a border portion (bonded portion) between the intermediate section 14 and the distal shaft 13.

The guide wire 2 shown in FIG. 1 is inserted to the inner shaft 11 from the distal end aperture of the distal end chip 111 serving as an inlet to the guide wire aperture 141 serving as an outlet. Radiopaque markers 121 are provided around the circumference of the inner shaft 11 in the balloon 12.

While not dilated, the balloon 12 is folded around the outer circumference of the inner shaft 11. When dilated, the balloon 12 will be formed such that the center portion becomes substantially cylindrical so as to be able to easily expand a stenosed portion of a blood vessel. It should be noted that the center portion of the balloon 12 is not necessarily be shaped into a complete cylinder, but may be into a polygonal column. Incidentally, the radiopaque markers 121 are provided to facilitate the positioning of the balloon 12 at the stenosed portion under fluoroscopy during angioplasty.

In the balloon catheter 1 having the above-described structure, as a pressure is applied by a pressure applying device (not shown) attached to the hub 16, a pressure medium is transferred from the hub 16 through the proximal shaft 15, the intermediate section 14, and a gap between the distal shaft 13 and the inner shaft 11, to reach the balloon 12, and thus the balloon 12 can be dilated. Needless to say, the proximal shaft 15, the intermediate section 14, the distal shaft 13, the inner tube shaft 11 and each of the bonded portions have pressure resistance higher than the pressure that bursts the balloon 12.

With reference to FIGS. 4A and 4B, the arrangement of the reinforcing member 142 in the intermediate section 14 will now be described in detail. In these figures, the intermediate section 14 is made of an inner layer 144 and an outer layer 143. Meanwhile, the reinforcing member 142 is made of a braided member in which a linear member or members are braided in lattice. The reinforcing member 142 is embedded between the inner layer 144 and the outer layer 143 of the intermediate section 14.

It should be noted that the intermediate section 14 need not always be of a two-layered structure, but it is possible that a reinforcing member 142 is embedded in an inner surface of the intermediate section 14 such as to be exposed to the inner lumen of the intermediate section 14.

When the reinforcing member 142 is embedded in the intermediate section 14 as described above, the intermediate section 14 becomes to have such rigidity that is lower (softer) than that of the proximal shaft 15 whereas higher (harder) than that of the distal shaft 13. Consequently, the rigidity varies stepwise from the proximal end to the distal end of the catheter 1. Thus, even if the intermediate section 14 is bent sharply, the stress is not concentrated in one point, thereby making it possible to reduce kink. Further, with this structure, the inner lumen of the intermediate section 14, that is, the cross section of the inflation lumen, can be maintained wide and the balloon inflation/deflation time can be shortened, unlike the conventional structure where a core wire is provided in the inner lumen of the intermediate section 14. Therefore, the time for stopping the blood flow during the balloon becomes short, and the stress on a patient can be suppressed to low level.

In such a rapid exchange type catheter as shown in these figures, it is preferable that the reinforcing member 14 should be provided to extend from the proximal end side of the intermediate section 14 to the distal end side, which is near the guide wire aperture 141. With this structure, the reinforcing member 142 reinforces the aperture 141 arranged distally apart from the proximal shaft 15, and thus it becomes possible to prevent kink or breakage of the aperture 141, which can be easily induced by the insertion or removal of the guide wire through the aperture 141. Further, in the proximal end side of the aperture 141, there is the guide wire present on an outer side of the catheter 1. Therefore, a relatively weak portion, which is not supported by the guide wire, is created between the proximal end of the aperture 141 and the distal end of the proximal shaft 15. However, as the braided member 142 is provided on this weak portion, unnecessary bending in the portion can be prevented, thereby making it possible to transmit surely torque or pushing force provided on the proximal end of the catheter to the distal shaft. Further, it is preferable that the reinforcing member 142 should not be extended to the distal end side to the aperture 141. In this manner, the portion on the distal end side to the aperture 141 can be made flexible, and therefore the catheter 1 can track to a peripheral part of a living body while accurately following up the curvature of its body cavity (blood vessel or the like). More specifically, it is preferable that the distal end of the reinforcing member 142 should be apart from the proximal end of the aperture 141 on the proximal side within a distance of 10 mm or less, more preferably 5 mm or less.

With reference to FIGS. 5A and 5B, another example of the arrangement of the reinforcing member 142 in the intermediate section 14 will now be described in detail. As shown in these figures, the reinforcing member 142 is formed by braiding a linear member or members such that there are sections where the inclination angles of the linear member constituting the reinforcement member 142 are relatively large (a section of an inclination angle $\alpha$) and relatively small (a section of an inclination angle $\beta$) with respect to the axial direction of the intermediate section 14. When the inclination angle with respect to the axial direction of the intermediate section 14 of the linear member is small, the orientation direction of the linear member becomes close to the axial direction of the catheter. In the section where the inclination angle is small, the reinforcing effect is enhanced, and the rigidity (especially, flexural rigidity and torsional rigidity) is improved. In order to fabricate such an intermediate section 14, it suffices only if the relative movement speed and/or relative rotational speed between the inner layer 144 and the linear member supplier are varied when linear members supplied from the linear member supplier of a braider (not shown) are spirally wound around the outer circumference of the inner layer 144. In this manner, the inclination angle of the linear member with respect to the axial direction of the intermediate section 14 can be varied continuously or stepwise. Consequently, it becomes possible to change the rigidity of the shaft gradually, thus enabling to even more effectively prevent the kink.

It should be noted that the reinforcing member 142 may be manufactured by using either a single linear member and an aggregate of linear members (for example, a strand formed by twisting linear members). Further, the reinforcing member 142 may be prepared by bundling a plurality of linear members together.

The material and size of each of the members which constitute the balloon catheter of the present invention will now be described in more detail.

For the proximal shaft 15, a material having a relatively high rigidity, for example, a metal such as Ni—Ti, brass, SUS and aluminum, should preferably be used. Here, a resin such as polyimide, vinyl chloride and polycarbonate can be used if it has relatively high rigidity.

The proximal shaft 15 is a tube with an outer diameter of 0.3 mm to 3 mm, preferably, 0.5 mm to 1.5 mm, a thickness of about 10 $\mu$m to 150 $\mu$m, preferably, 20 $\mu$m to 100 $\mu$m, and a length of 300 mm to 2000 mm, preferably 700 mm to 1500 mm.

The distal shaft 13 and the intermediate section 14 may be made of a properly formed single tube, or a tube for the distal shaft and a tube for the intermediate section may be prepared separately, and then bounded together appropriately.

Examples of the material which constitutes the distal shaft 13 and the intermediate section 14 are high-molecular materials including polyolefin (such as polyethylene, polypropylene, polybutene, ethylene-propylene co-polymer, ethylene-vinyl acetate copolymer, ionomer, or a mixture of at least two types thereof), cross-linked polyolefin, polyvinyl chloride, polyamide, polyamide elastomer, polyester, polyester elastomer, polyurethane, polyurethane elastomer, fluorinated resin, and polyimide, and a mixture thereof.

Each of the distal shaft 13 and the intermediate section 14 is a tube with an outer diameter of 0.5 mm to 1.5 mm, preferably, 0.7 mm to 1.1 mm, a thickness of about 25 $\mu$m to 200 $\mu$m, preferably, 50 $\mu$m to 100 $\mu$m, and a length of 300 mm to 2000 mm, preferably 300 mm to 1500 mm.

The reinforcing member 142 embedded in the intermediate section 14 is made of a linear member having an outer diameter of 10 $\mu$m to 80 $\mu$m, preferably, 20 $\mu$m to 50 $\mu$m. The material for the reinforcing member 142 is not particularly limited as long as it has such rigidity that can obtain a sufficient reinforcing effect. For example, various types of metal materials, such as stainless steel, copper, tungsten, neckel, titanium, piano wire, Ni—Ti alloy, Ni—Ti—Co alloy, Ni—Al alloy, Cu—Zn alloy, a superelastic alloy such as Cu—Zn—X (X is, for example, Be, Si, Sn, Al or Ga), and amorphous alloy, can be used. Further, polyester such as polyethylene telephthalate (PET) and polybuthylene telephthalate (PBT), polyolefin such as polyethylene and polypropylene, hard polyvinyl chloride, polyamide, polyimide, polystylene, thermo plastic polyurethane, polycarbonate, ABS resin, acrylic resin, polymethyl methacrylate (PMMA), polyacetal (PA), polyallylate, polyoxymethylene (POM), high-tensile polyvinyl alcohol, fluorinated resin, polyvinylidene fluoride (PVDF), polytetrafluoroethylene, saponificated ethylene-vinylacetate (EVOH), polysulfone, polyether sulfone, polyether ketone, polyphenylene oxide, polyphenylene sulfide, polymer alloy containing anyone of these, carbon fiber, glass fiber, and combination of two or more of these, can be used. It should be noted that of these materials, stainless steel, PET and the like are more preferable for the reasons of high processability, being economical and non-toxic.

The material which constitutes the inner tube shaft 11 should be of a type having flexibility of some degree, and examples of the material are polymer materials including polyolefin (such as polyethylene, polypropylene, polybutene, ethylene-propylene copolymer, ethylene-vinyl acetate copolymer ionomer and a mixture thereof), a cross-linked polyolefin, polyvinyl chloride, polyamide, polyamide elastomer, polyester, polyester elastomer, polyurethane, polyurethane elastomer, polyimide, fluorinated resin, and a mixture thereof.

The inner shaft 11 is a tube with an outer diameter of 0.1 mm to 1.0 mm, preferably, 0.3 mm to 0.7 mm, a thickness of about 10 $\mu$m to 150 $\mu$m, preferably, 20 $\mu$m to 100 $\mu$m, and a length of 100 mm to 2000 mm, preferably 200 mm to 1500 mm.

The material which constitutes the balloon 12 should be of a type having a flexibility of some degree so as to be dilatable constricted portions in a blood vessel. Examples of the material are polymer materials including polyolefin (such as polyethylene, polypropylene, polybutene, ethylene-propylene copolymer, ethylene-vinyl acetate copolymer and ionomer), a cross-linked polyolefin, polyester (such as polyethyleneterephthalate), polyester elastomer, polyvinyl chloride, polyurethane, polyurethane elastomer, polyphenylenesulfide, polyamide (such as nylon), polyamide elastomer, fluorinated resin, and a mixture thereof, silicone rubber and latex rubber. Also, a laminated film made by appropriately laminating these polymer materials can be used. Alternatively, it is possible to have a structure in which a balloon 12 made by a biaxially stretching blow molding is mounted on a distal end side of the distal shaft 13, or the distal end portion of the distal shaft 13 is subjected to stretching blow molding to form the balloon 12 in an integral body.

The balloon 12 has a shape with an outer diameter of a cylindrical portion when inflated, of 1.0 mm to 10 mm, preferably, 1.0 mm to 5.0 mm, a length of 5 mm to 50 mm, preferably 10 mm to 40 mm, and an entire length of 10 mm to 70 mm, preferably 15 mm to 60 mm.

The radiopaque marker 12 should be made of a coil spring or a ring, and two or more of such radiopaque markers 12 can be provided. Preferable examples of the material for the radiopaque maker 12 are those having high radiopaque properties, such as Pt, Pt alloy, W, W alloy, Au, Au alloy, Ir, Ir alloy, Ag, and Ag alloy.

In the above description, the present invention has been described in connection with the case of a rapid-exchange type catheter having a guide wire aperture 141 at a position distant from the proximal end of the catheter in the direction of the distal end side; however the present invention is not limited to this type, but it may be of a type in which the guide wire aperture is formed at a proximal end portion (for example, in the hub) of the catheter.

Further, the embodiment shown in the figures is catheter having a coaxial structure in which the guide wire lumen is coaxially disposed within the distal shaft; however the present invention is not limited to this type, but it may be of a type in which the lumen for the guide wire and the lumen for balloon inflation are formed in parallel with each other.

As described above, with the catheter of the present invention, the cross section of the inflation lumen is not narrowed or the balloon inflation/deflation time is not prolonged accordingly, unlike so in the conventional case where a core wire is used, and therefore the stress on a patient can be suppressed to low level. Further, the reinforcing member consisting of a braided member exhibits a more significant kink resistance than the reinforcing member made of the conventional coil member. Furthermore, if the reinforcing member is made by braiding such that there are sections where the inclination angles of the linear member constituting the reinforcement member are relatively large and relatively small with respect to the axial direction of the intermediate section, the rigidity of the shaft can be gradually changed. Consequently, the kink can be more efficiently avoided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A balloon catheter comprising:
   a tubular proximal shaft having relatively high rigidity;
   a tubular distal shaft having rigidity lower than that of the proximal shaft;
   a tubular intermediate section disposed between the proximal shaft and the distal shaft;
   a hub arranged near a proximal end of the proximal shaft, to which a pressure applying apparatus is attached;

a balloon provided to a distal portion of the distal shaft to be in fluid communication, to which pressure is applied from the hub; and a guide wire lumen having a distal aperture located on a distal end side of the distal end of the balloon and a proximal aperture located on a proximal end side of the proximal end of the balloon, through which a guide wire is inserted;

wherein a reinforcing member consisting of a braided member formed by braiding at least one linear member, is embedded in the intermediate section, by which rigidity of the intermediate section is made lower than that of the proximal shaft and higher than that of the distal shaft.

2. The balloon catheter according to claim 1, wherein the proximal shaft is made of a metal tube.

3. The balloon catheter according to claim 1, wherein the intermediate section includes an inner layer and an outer layer, and the reinforcing member is embedded between the inner layer and the outer layer of the intermediate section.

4. The balloon catheter according to claim 1, wherein the reinforcing member is embedded in the intermediate section such that it is exposed to the inner lumen of the intermediate section.

5. The balloon catheter according to claim 1, wherein the reinforcing member has sections where the inclination angles of the linear member constituting the reinforcement member are relatively large and relatively small with respect to the axial direction of the intermediate section.

6. The balloon catheter according to claim 1, further comprising an inner shaft provided coaxially within the distal shaft, wherein the guide wire lumen is created by an inner lumen of the inner shaft.

7. The balloon catheter according to claim 1, wherein the proximal aperture is located on a distal end side of the distal end of the proximal shaft, and the reinforcing member is extending from a proximal portion of the intermediate section to near the proximal aperture.

8. A catheter comprising:

a proximal shaft having relatively high rigidity; a distal shaft having rigidity lower than that of the proximal shaft;

an intermediate section disposed between the proximal shaft and the distal shaft;

a hub arranged near a proximal end of the proximal shaft;

a treatment device attached on a distal portion of the distal shaft; and a guide wire lumen having a distal aperture located on a distal end side of the treatment device and a proximal aperture located on a proximal end side of the proximal end of the treatment device, through which a guide wire is inserted;

wherein a reinforcing member consisting of a braided member formed by braiding at least one linear member, is embedded in the intermediate section, by which rigidity of the intermediate section is made lower than that of the proximal shaft and higher than that of the distal shaft.

9. The catheter according to claim 8, wherein the proximal shaft is made of a metal tube.

10. The catheter according to claim 8, wherein the intermediate section includes an inner layer and an outer layer, and the reinforcing member is embedded between the inner layer and the outer layer of the intermediate section.

11. The catheter according to claim 8, wherein the reinforcing member is embedded in the intermediate section such that it is exposed to the inner lumen of the intermediate section.

12. The catheter according to claim 8, wherein the reinforcing member has sections where the inclination angles of the linear member constituting the reinforcement member are relatively large and relatively small with respect to the axial direction of the intermediate section.

13. The catheter according to claim 8, further comprising an inner shaft provided coaxially within the distal shaft, wherein the guide wire lumen is created by an inner lumen of the inner shaft.

14. The catheter according to claim 8, wherein the proximal aperture is located on a distal end side of the distal end of the proximal shaft, and the reinforcing member is extending from a proximal portion of the intermediate section to near the proximal aperture.

15. The balloon catheter according to claim 7, wherein the distal end of the reinforcing member including a braided member is apart from the proximal end of the proximal aperture on the proximal side within a distance of 10 mm or less.

16. The catheter according to claim 14, wherein the distal end of the reinforcing member including a braided member is apart from the proximal end of the proximal aperture on the proximal side within a distance of 10 mm or less.

\* \* \* \* \*